United States Patent
Nagai et al.

(10) Patent No.: US 7,248,997 B2
(45) Date of Patent: Jul. 24, 2007

(54) DRIVER'S CONDITION DETECTOR FOR VEHICLE AND COMPUTER PROGRAM

(75) Inventors: Fumiya Nagai, Anjo (JP); Teiyuu Kimura, Nagoya (JP); Katsuyoshi Nishii, Okazaki (JP); Kazuhiro Sakai, Anjo (JP)

(73) Assignee: DENSO Corporation, Kariya (JP)

( * ) Notice: Subject to any disclaimer, the term of this patent is extended or adjusted under 35 U.S.C. 154(b) by 11 days.

(21) Appl. No.: 11/113,988

(22) Filed: Apr. 26, 2005

(65) Prior Publication Data

US 2005/0246134 A1  Nov. 3, 2005

(30) Foreign Application Priority Data

Apr. 28, 2004 (JP) .............................. 2004-133974

(51) Int. Cl.
*G06F 11/30* (2006.01)
(52) U.S. Cl. .................................... 702/182
(58) Field of Classification Search ................ 702/182; 340/576, 575
See application file for complete search history.

(56) References Cited

U.S. PATENT DOCUMENTS

| | | | | |
|---|---|---|---|---|
| 6,661,345 B1 * | 12/2003 | Bevan et al. | ............... | 340/575 |
| 6,974,414 B2 * | 12/2005 | Victor | ........................ | 600/300 |
| 2002/0140562 A1 * | 10/2002 | Gutta et al. | ................. | 340/576 |
| 2003/0043045 A1 * | 3/2003 | Yasushi et al. | ............. | 340/576 |
| 2003/0146841 A1 * | 8/2003 | Koenig | ........................ | 340/576 |
| 2004/0046666 A1 * | 3/2004 | Yasuchi | ................... | 340/573.1 |
| 2004/0054452 A1 * | 3/2004 | Bjorkman | ..................... | 701/29 |
| 2004/0090334 A1 * | 5/2004 | Zhang et al. | ................ | 340/575 |
| 2004/0124985 A1 * | 7/2004 | Young et al. | ................ | 340/575 |
| 2005/0159851 A1 * | 7/2005 | Engstrom et al. | ............... | 701/1 |

FOREIGN PATENT DOCUMENTS

JP  A-H11-314534  11/1999

* cited by examiner

*Primary Examiner*—John Barlow
*Assistant Examiner*—Xiuqin Sun
(74) *Attorney, Agent, or Firm*—Posz Law Group, PLC

(57) ABSTRACT

A driver's condition detection device is for detecting a first life information indicating a driver's degree of activity. The driver's condition classification device is for classifying the first life information into at least two regions. The driver's condition determination device is for determining the driver's condition based on a distribution of the first life information in the regions.

38 Claims, 10 Drawing Sheets

| QUAD. | VEHICLE | LIFE | RISK | ACTIVITY AROUSAL |
|---|---|---|---|---|
| A | ACTIVE | ACTIVE | LOW | HIGH |
| B | INACTIVE | ACTIVE | ↓ | ↓ |
| C | INACTIVE | INACTIVE | ↓ | ↓ |
| D | ACTIVE | INACTIVE | HIGH | LOW |

(1) HR. SD
(2) HR. CV (= (HR. SD/HR. Ave) × 100)
(3) a × HR. SD + b × HR. Ave
(4) a × HR. SD + b × (HR. Ave − HR. Ave')
(5) k × HR. SD × HR. Ave
(6) k × HR. SD × (HR. Ave − HR. Ave')

(1) ACCELERATION (A.) SD
(2) VELOCITY (V.) SD
(3) V. CV (= (V. SD/V. Ave) × 100)
(4) a × A. SD + b × V. Ave
(5) a × V. SD + b × V. Ave
(6) a × V. CV + b × V. Ave
(7) k × A. SD × V. Ave
(8) k × V. SD × V. Ave (1) ACCELERATION (A.) SD
(2) VELOCITY (V.) SD
(3) V. CV (= (V. SD/V. Ave) × 100)
(4) a × A. SD + b × V. Ave
(5) a × V. SD + b × V. Ave
(6) a × V. CV + b × V. Ave
(7) k × A. SD × V. Ave
(8) k × V. SD × V. Ave

FIG. 6

| | INFO. SOURCE | SAFE | CAUTIONARY | WEIGHTING |
|---|---|---|---|---|
| 2nd VEHICLE INFO. | OUTER (COMPARTMENT) TEMP. SENSOR | MODERATE | HOT (WARM) | A |
| | GPS INFO. | URBAN AREA | EXP. WAY (MONOTONOUS ROAD) | B |
| | VICS INFO. | FLOWING | CONGESTED | C |
| | CONT. TRAVEL TIME | SHORT | LONG | D |
| | CONT. TRAVEL DIST. | SHORT | LONG | E |
| | RAIN SENSOR | NOT RAINING | RAINING | F |
| | PASSENGER DETECTOR | WITH PASSENGER | DRIVER ONLY | G |
| | AUDIO (RADIO) | ON | OFF | H |
| | CALENDAR (TIME) | DAY | NIGHT | I |
| | CARRYING LOAD | SMALL | LARGE | J |
| 2nd LIFE INFO. | QUALITY OF LAST SLEEP | GOOD | BAD | K |
| | PHYS. COND. PRED. | GOOD | BAD | L |
| | CIRCADIAN RHYTHM | HIGH | LOW (NIGHT) | M |
| THRESHOLD | LIFE INFO. | SMALL | LARGE | — |
| | TIME (FREQUENCY) | LARGE | SMALL | — |

DRIVER'S CONDITION DETECTOR FOR VEHICLE AND COMPUTER PROGRAM

CROSS REFERENCE TO RELATED APPLICATION

This application is based on Japanese Patent Application No. 2004-133974 filed on Apr. 28, 2004, the content of which is incorporated herein by reference.

FIELD OF THE INVENTION

The present invention relates to a driver's condition detector capable of measuring a driver's degree of activity such as an arousal and an attention of a driver of a vehicle and a computer program for realizing the driver's condition detector.

BACKGROUND OF THE INVENTION

A driver's fatigue caused such by driving operation for a long time may increase a risk of a traffic accident. Currently, an apparatus is under development for detecting a driver's degree of fatigue to prevent the traffic accident.

JP-11-314534-A (Page 2, FIG. 7) discloses an apparatus for detecting the driver's degree of fatigue, which identifies a driver, detects a heart rate of the driver and determines the driver's degree of fatigue based on a variation of the heart rate.

However, according to the above-described prior art, the driver's physical condition and/or the daily variation of the driver's physical condition is not taken into account for determining the driver's degree of fatigue. Thus, the apparatus cannot determine the driver's condition with high accuracy. Further, the above-described apparatus includes an ambiguity in determining when to generate an alarm to notify the driver's fatigue.

SUMMARY OF THE INVENTION

The present invention is achieved in view of the above-described issues and has an object to provide a driver's condition detector for a vehicle and a computer program for realizing the driver's condition detector capable of determining a driver's condition such as a degree of activity with high accuracy and generating an alarm at a proper timing to notify the driver of the driver's condition unsuitable for driving operation.

To achieve the above-described object, the driver's condition detector for a vehicle has a driver's condition detection device, a driver's condition classification device and a driver's condition determination device.

The driver's condition detection device is for detecting a first life information indicating a driver's degree of activity. The driver's condition classification device is for classifying the first life information into at least two regions. The driver's condition determination device is for determining the driver's condition based on a distribution of the first life information in the regions.

BRIEF DESCRIPTION OF THE DRAWINGS

Features and advantages of embodiments will be appreciated, as well as methods of operation and the function of the related parts, from a study of the following detailed description, the appended claims, and the drawings, all of which form a part of this application. In the drawings:

FIG. 6 is a table showing weightings of a second life information and a second vehicle information used for determining a life information threshold and the time domain threshold in the first embodiment;

DETAILED DESCRIPTION OF PREFERRED EMBODIMENTS (a) Firstly, a system configuration of the driver's condition detector according to a first embodiment of the present invention will be described with reference to FIG. 1. As shown in FIG. 1, a vehicle (car) mounts the driver's condition detector 1 thereon which is realized in an electric control unit (ECU) having a main portion of a conventional microcomputer.

Figure 1:
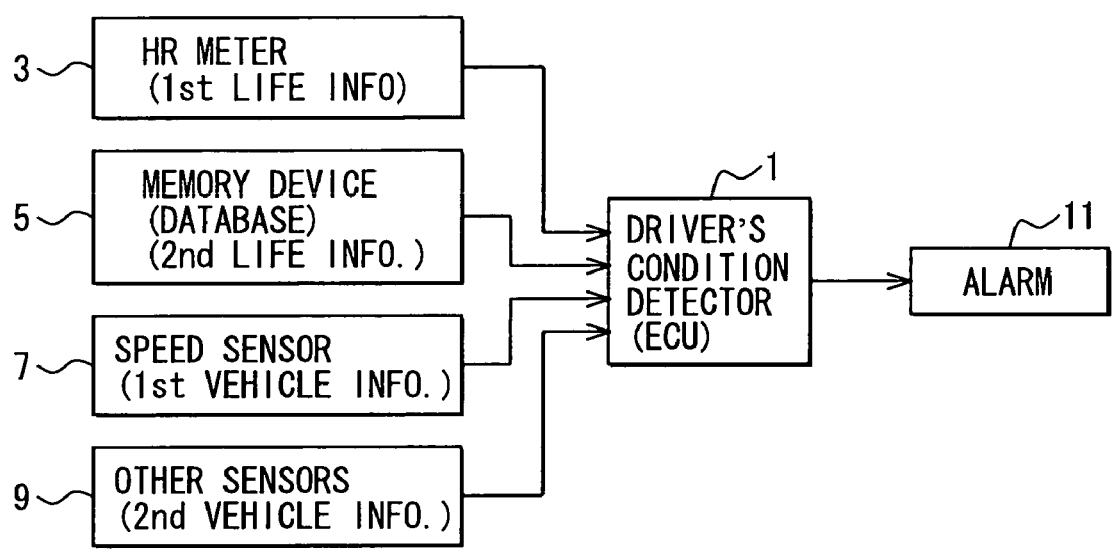
FIG. 1 is a block diagram showing a system configuration of a driver's condition detector for a vehicle according to a first embodiment of the present invention.

The driver's condition detector 1 receives signals sent from a pulsation sensor 3 by a wired communication or a wireless communication.

Further, a memory device 5 such as an electrically erasable programmable ROM (EEPROM) and a hard disk drive stores a database of a second life information concerning the driver's condition. The memory device 5 provides the driver's condition detector 1 with the second life information necessary for determining a threshold values that will be described below.

As shown in FIG. 6, the second life information in the database includes a driver's latest sleep quality, a data for predicting a driver's condition, a standard division of the heart rate HR.SD in a driver's usual sleep, a daily circadian rhythm of a driver's heart rate, etc. (that is, a variation of the driver's heart rate throughout a day), a weekly circadian rhythm of the same, a yearly circadian rhythm of the same and so on.

Further, a speed sensor 7 such for a digital tachometer and a car navigation system provides the driver's condition detector 1 with a vehicle speed data as a first vehicle information. The driver's condition detector 1 calculates a vehicle's acceleration and so on based on the vehicle speed data.

Further, other kinds of sensors 2 mounted on the vehicle provide the driver's condition detector with a second vehicle information.

As shown in FIG. 6, the second vehicle information includes a driver's latest sleep quality, a data for predicting a driver's condition, a standard division of the heart rate HR.SD in a driver's usual sleep, a daily circadian rhythm of a driver's heart rate, etc. (that is, a variation of the driver's heart rate throughout a day), a weekly circadian rhythm of the same, a yearly circadian rhythm of the same and so on.

Thus, the driver's condition detector 1 obtains the first and second life information and the first and second vehicle information, then calculates threshold values such as a life information threshold value and a vehicle information threshold value for classifying domains to determine the driver's activity with the second life information and the second vehicle information. Further, the driver's condition detector 1 determines the domains to separate the drivers activity with the threshold values, then determines how suitable is the driver's activity such as the driver's sleepiness and attention for driving.

When the driver's condition detector 1 determines that the driver's activity is not enough for driving, the driver's condition detector 1 actuates an alarm device 11, etc., to alarm the driver by generating a sound, voice, a display on an indicator, a wind, a vibration and so on.

Figures 2A, 2B:
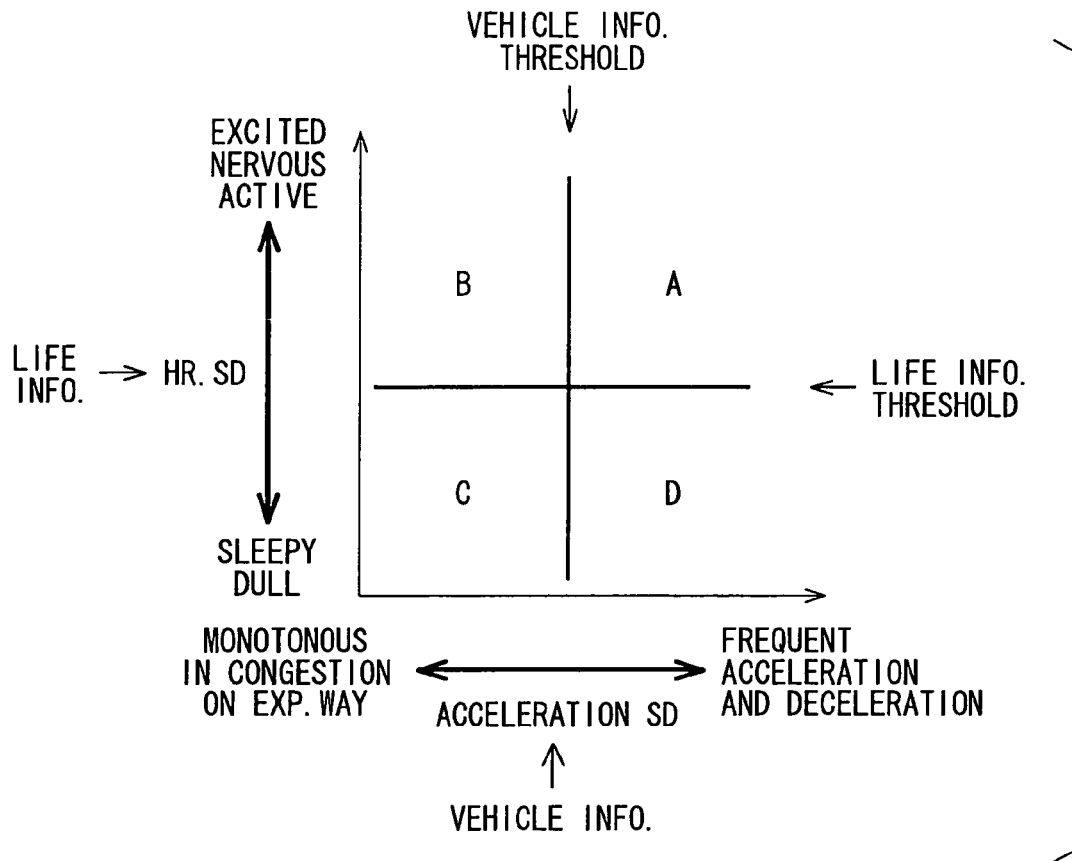
FIG. 2A is a schematic diagram showing a classification of a driver's degree of activity in accordance with a vehicle's degree of action according to the first embodiment.
FIG. 2B is a table showing a classification of the driver's degree of activity and the vehicle's degree of action according to the first embodiment.

(b) Classification of the driver's degree of activity will be described.

i) An ordinate in FIG. 2A denotes the standard division of a driver's heart rate HR.SD. An upper side of FIG. 2A means a relatively large heart rate (excite, nervous or active state) and a lower side thereof means a relatively small heart rate (sleepy or dull state).

An abscissa in FIG. 2A denotes the standard division of the vehicle acceleration A.SD. A right side of FIG. 2A means a relatively large heart rate (excite, nervous or active state) and a left side thereof means a relatively small heart rate (sleepy or dull state).

As shown in FIG. 2B, a predetermined life information threshold and a predetermined vehicle information threshold classify the driver's degree of activity into four quadrants A-D. In the quadrant A, the vehicle's motion and the driver's condition are active. In the quadrant B, the vehicle's motion is monotonous and the driver's condition is active. In the quadrant C, the vehicle's motion is monotonous and the driver's condition is inactive. In the quadrant D, the vehicle's motion is active whereas the driver's condition is inactive.

Figure 3:
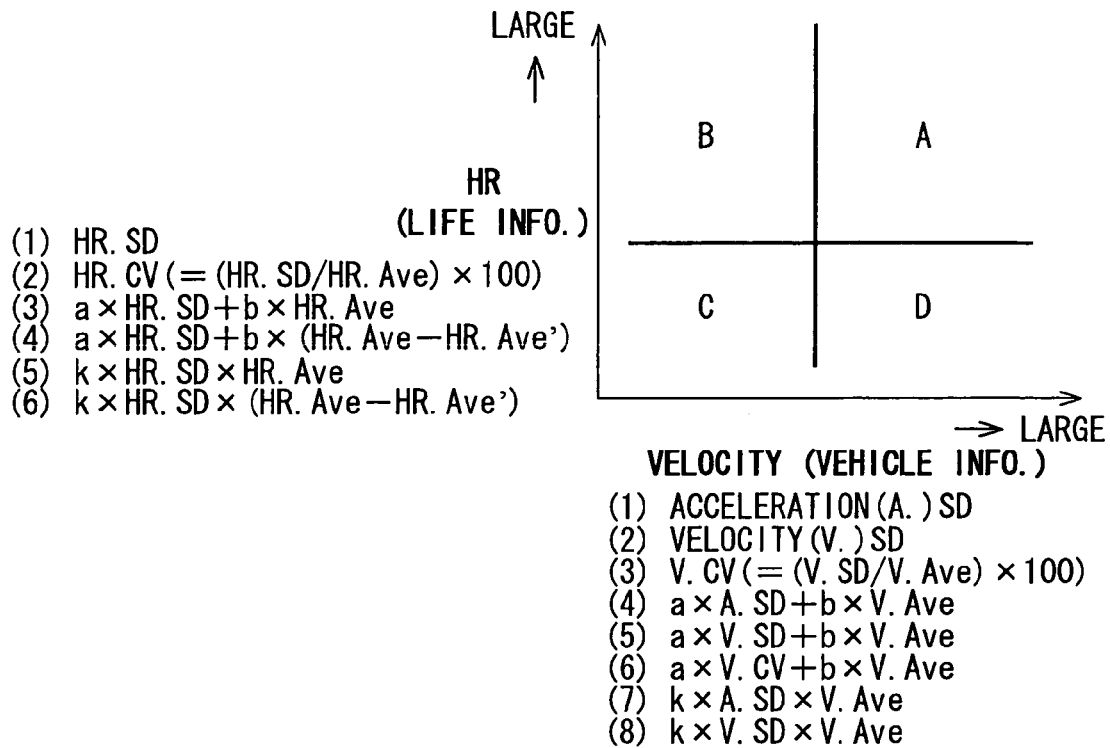
FIG. 3 is the schematic diagram of FIG. 2A showing indicators of the driver's degree of activity and the vehicle's degree of action.

Thus, the driver's degree of activity (arousal) decreases and the driving risk increases in a order of the quadrant A, B, C and D.

ii) A classification of the driver's degree of activity can employ quadrants shown in FIG. 3.

In FIG. 3, an ordinate indicates the life information correlated with the driver's heart rate HR. An Indicator of the life information can employ any one of the values (1) to (6) below in each analytic segment (data obtained for one minute, for example).

(1) HR.SD;
(2) HR.CV=(HR.SD/HR.Ave)×100;
(3) a×HR.SD+b×HR.Ave;
(4) a×HR.SD+b×(HR.Ave−HR.Ave');
(5) k×HR.SD×HR.Ave; and
(6) k×HR.SD×(HR.Ave−HR.Ave'), wherein HR.SD denotes a standard division of the driver's heart rate in the analytic segment, HR.CV denotes a coefficient of the heart rate variation, HR.Ave denotes a driver's average heart rate in the analytic segment, "a" and "b" denote weightings, HR.Ave' denotes a driver's average heart rate at a predetermined condition and "k" denotes a coefficient.

The above-described driver's average heart rate HR.Ave' at a predetermined condition can employ the driver's average heart rate in a daytime, in a period of several minutes just after starting a travel in which the driver is certainly aware and so on. Further, by measuring the driver's heart rate regularly, the driver's average heart rate HR.Ave' at a predetermined condition contains daily, weekly and yearly variations of the driver's heart rate. For example, when traveling home, it is useful that the driver's average heart rate HR.Ave' employs a stored driver's average heart rate detected when the driver was traveling home before. When traveling on Wednesday, it is useful that the driver's average heart rate HR.Ave' employs a stored driver's average heart rate detected on Wednesday before.

Figure 4:
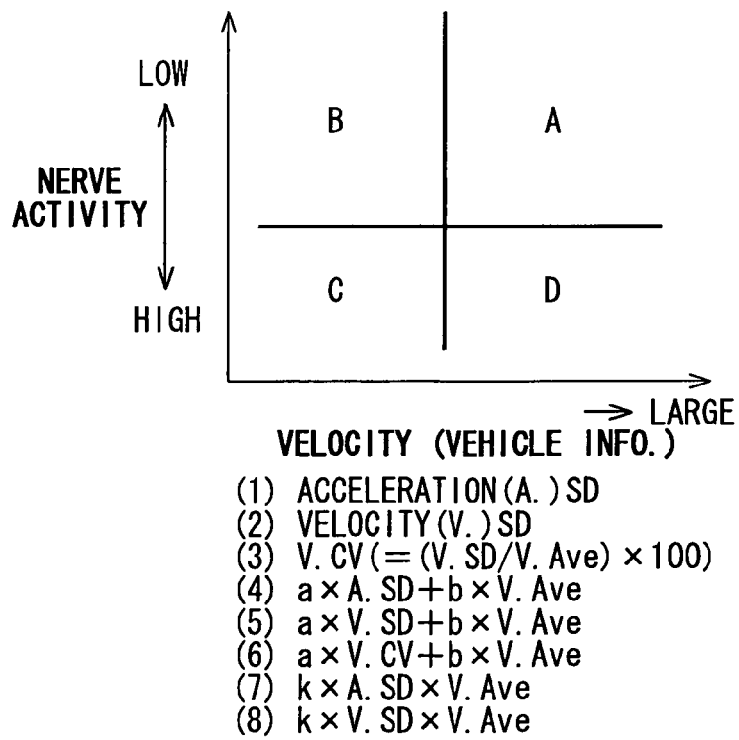
FIG. 4 is the schematic diagram of FIG. 2A showing other indicators of the driver's degree of activity and the vehicle's degree of action.

Regardless of the above description, as shown in FIG. 4, the ordinate may indicate a driver's nerve activity such as a fluctuation of the driver's heart rate. When the driver's nerve activity is high, the driver's condition is relaxed and in the quadrant C or D. When the driver's nerve activity is low, the driver's condition is tense and in the quadrant A or B.

In FIGS. 3 and 4, the abscissa indicates the vehicle information correlated with the vehicle's velocity and acceleration. An indicator of the vehicle information can employ any one of the values (1) to (8) in each analytic segment (data obtained for one minute, for example).

Figure 5A:
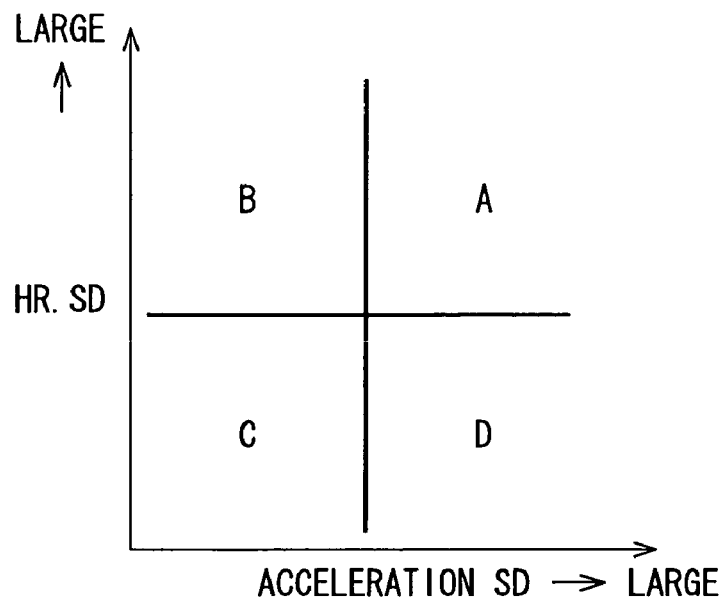
FIG. 5A is a schematic diagram showing another classification of the driver's degree of activity and the vehicle's degree of action employing a time domain threshold according to the first embodiment.
Figure 5B:
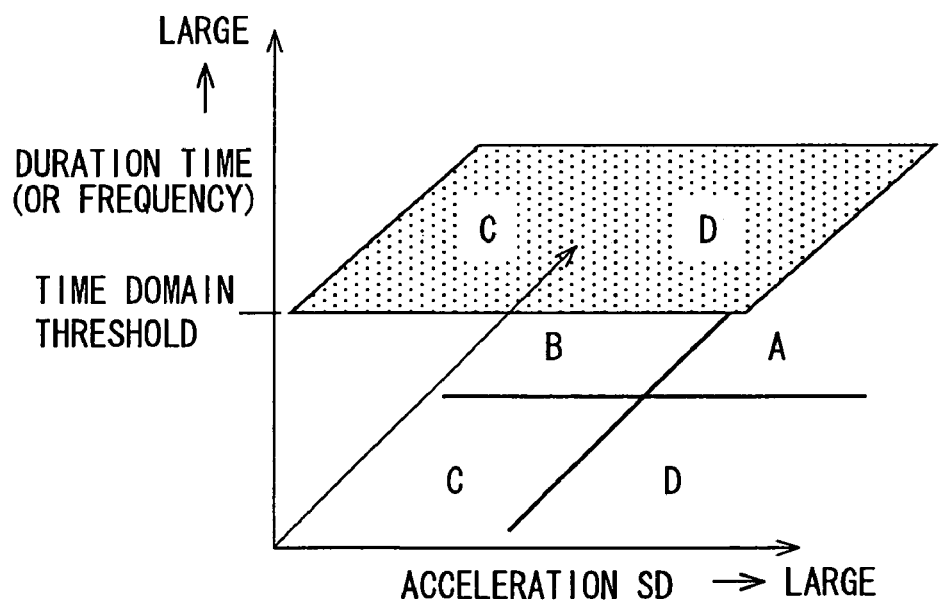
FIG. 5B is a schematic diagram showing another classification of the driver's degree of activity and the vehicle's degree of action employing a time domain threshold according to the first embodiment.

(1) A.SD;
(2) V.SD;
(3) V.CV=(V.SD/V.Ave)×100;
(4) a×A.SD+b×V.Ave;
(5) a×V.SD+b×V.Ave;
(6) a×V.CV+b×V.Ave;
(7) k×A.SD×V.Ave; and
(8) k×V.SD×V.Ave, wherein A.SD denotes a standard division of the vehicle's acceleration in the analytic segment, V.SD denotes a standard division of the vehicle's velocity, V.CV denotes a coefficient of the vehicle's velocity variation, V.Ave denotes a vehicle's average velocity in the analytic segment, "a" and "b" denote weightings and "k" denotes a coefficient.

iii) A three-dimensional classification of the driver's degree of activity is shown in FIGS. 5A and 5B.

Specifically, a time axis (a Z-axis) is adopted perpendicular to the abscissa (X-axis) and the ordinate (Y-axis) as shown in FIG. 5B. The time axis indicates a duration time in which the driver's condition continuously remains in the quadrants C and D, namely the driver's degree of activity is relatively low. The time domain indicated by the time axis is classified into a longer region and a shorter region by a time domain threshold determined by the ECU 1 based on the second life information and/or the second vehicle information as shown in FIG. 6 for example. The duration time may be alternated with a frequency for the driver's condition to be in the quadrant C or D.

That is, the longer the duration time is in which the driver's condition remains in quadrant C or D, namely the longer the driver's degree of activity remains low to be unsuitable for driving, the higher the degree of driving risk is. The time domain threshold set in the time axis is useful for detecting the degree of driving risk with high accuracy. When the Z-axis indicates the frequency, the ECU 1 can detect the degree of driving risk by the frequency for the driver's condition to be in the quadrant C or D, for example how many minutes the driver's condition has been in a predetermined period ΔT.

When the duration time or the frequency is over the time domain threshold, the driver's condition remains low for a long period. In this case, the ECU 1 generates an alarm to notify the driver of the cautionary and unsuitable condition for driving.

When the driver's condition moves between the quadrants C and D, the duration time can be added together.

iv) In this embodiment, the ECU 1 adjusts the life information threshold set in the ordinate and the time domain threshold set in the time axis based on a second life information and a second vehicle information shown in FIG. 6.

The threshold value for the first vehicle information can employ a predetermined value. Specifically, as shown in FIG. 6, the ECU 1 obtains information from respective information sources such as sensors and classifies each kind of the information into one indicating a safe state and another indicating a cautionary state. Then the ECU 1 determines weightings (importance) for each kind of the information to determine and adjust the life information threshold and the time domain threshold.

For example, when the second vehicle information employs an outer temperature, the ECU 1 determines whether the outer temperature is moderate or hot. If hot, the ECU 1 sets the life information threshold relatively large and the vehicle information threshold relatively small. The large life information threshold extends the area of the quadrants C and D. When the time domain threshold is small, the ECU 1 generates an alarm when the driver's condition remains in the quadrant C or D only for a short period.

Thus, the large information threshold increases a frequency and/or the duration time for the driver's condition to be in the quadrants C or D. The duration time of the driver's condition in the quadrants C and D reaches the time domain threshold in a relatively small period. As a result, the ECU 1 generates an alarm earlier.

Here, the life information threshold and/or the time domain threshold may be determined based on any one of the information sources of the second vehicle information and the second life information shown in FIG. 6. The life information threshold and/or the time domain threshold may be determined based on a plurality of the information sources.

When the ECU 1 determines the life information threshold and/or the time domain threshold based on a plurality of the information sources, it is useful to adopt weightings for each the plurality of the information sources as shown in a following equation (1).

$$(\text{The threshold}) = A \times (\text{outer temperature}) + B \times (\text{GPS information}) + C \times (\text{VICS information}) + \quad (1)$$

v) Furthermore, the ECU 1 estimates the driver's condition based on the driver's heart rate HR measured by the heart rate sensor 3.

Figure 7A:
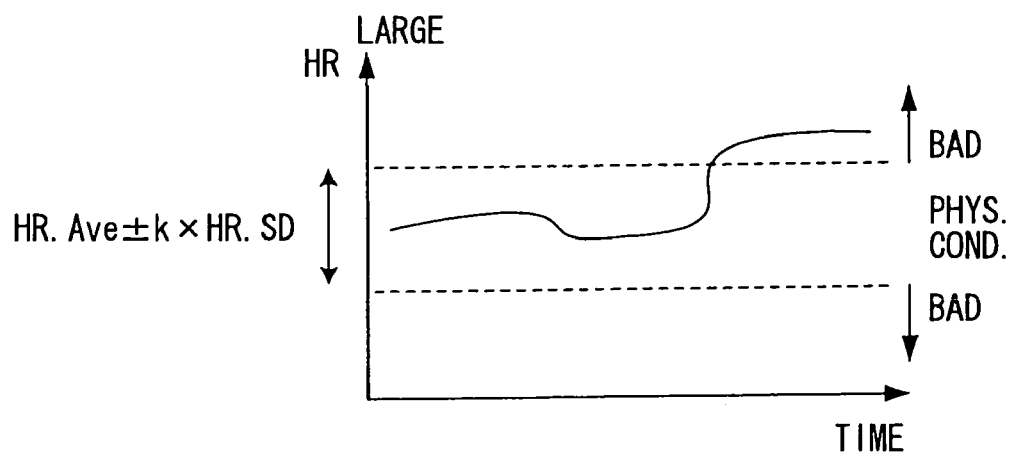
FIG. 7A is a schematic graph showing a method for determining a driver's condition according to the first embodiment.

As shown in FIG. 7A, when the driver's heart rate HR is in a predetermined desirable range (HR.Ave±k×HR.SD; wherein k denotes a coefficient), the ECU 1 determines the driver is physically in a good condition. When the driver's heart rate HR is out of the predetermined desirable range, the ECU 1 determines the driver is physically in a bad condition.

Figure 7B:
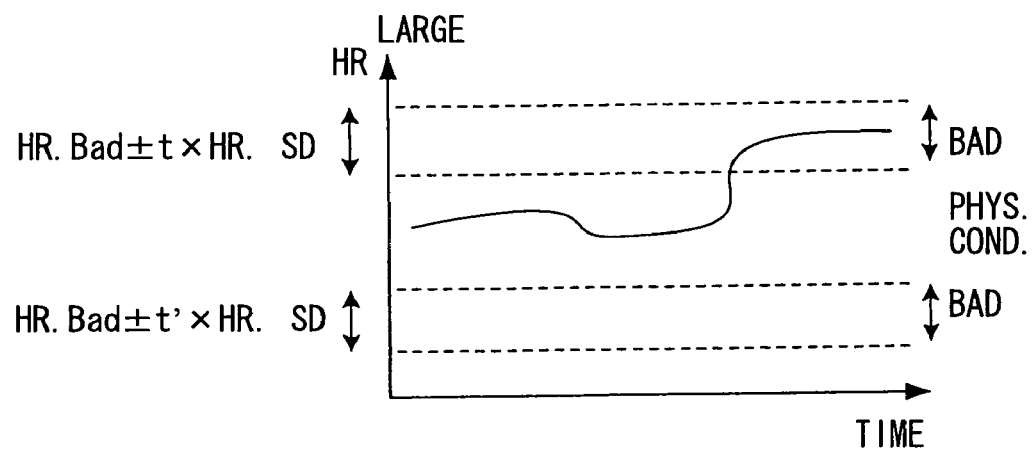
FIG. 7B is a schematic graph showing another method for determining a driver's condition according to the first embodiment.

Further, as shown in FIG. 7B, when the driver's heart rate HR is in a predetermined undesirable range (HR.Bad±t (or t')×HR.SD; wherein HR.Bad denotes a driver's heart rate registered in a physically bad condition and t or t' denotes a coefficient), the ECU 1 determines the driver is in a physically bad condition. When the driver's heart rate HR is out of the predetermined desirable range, the ECU 1 determines the driver is in a good condition.

The ECU 1 sets the above-described threshold values in view of a result of the above-described estimation of the driver's condition as the weightings in FIG. 6. Thus, the driver's condition detector 1 can detect the driver's condition with high accuracy.

(c) The process done by the driver's condition detector 1 will be described.

Figure 8:
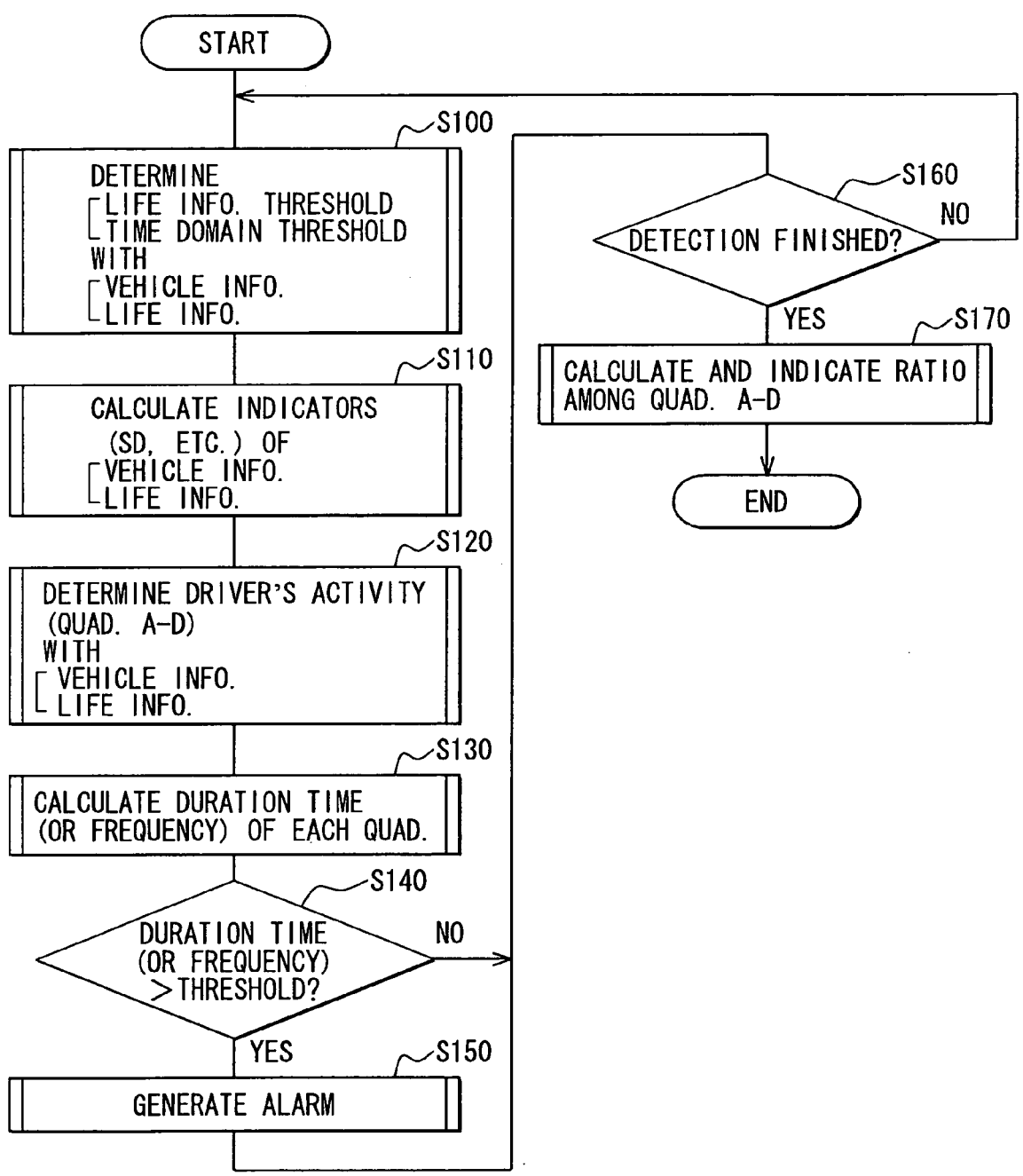
FIG. 8 is a flowchart showing a process of the driver's condition detector for a vehicle according to the first embodiment.
Figure 9A:
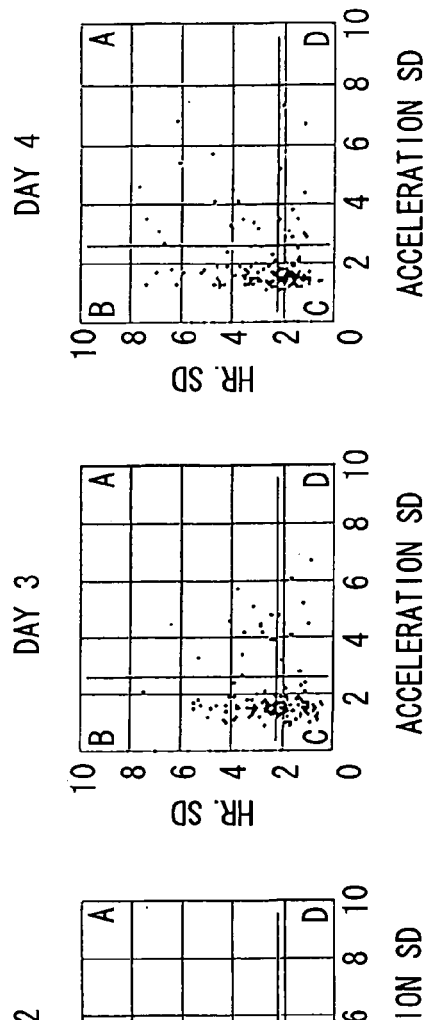
FIG. 9A is a graph showing a distribution of the driver's degree of activity according to the present invention.
Figure 9B:
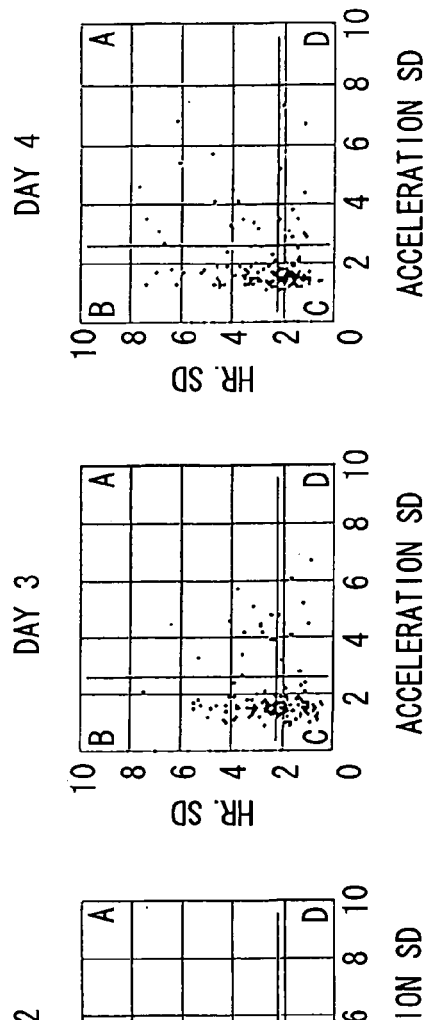
FIG. 9B is a graph showing a distribution of the driver's degree of activity according to the present invention.
Figure 9C:
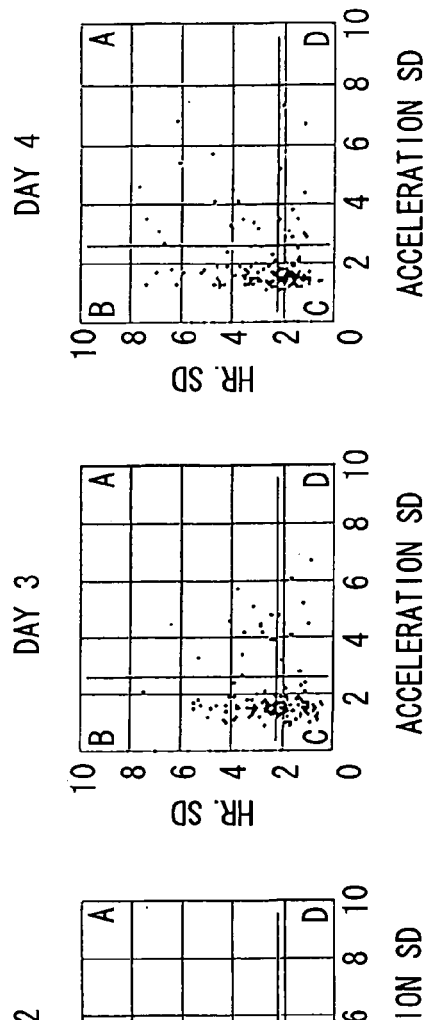
FIG. 9C is a graph showing a distribution of the driver's degree of activity according to the present invention.
Figure 9D:
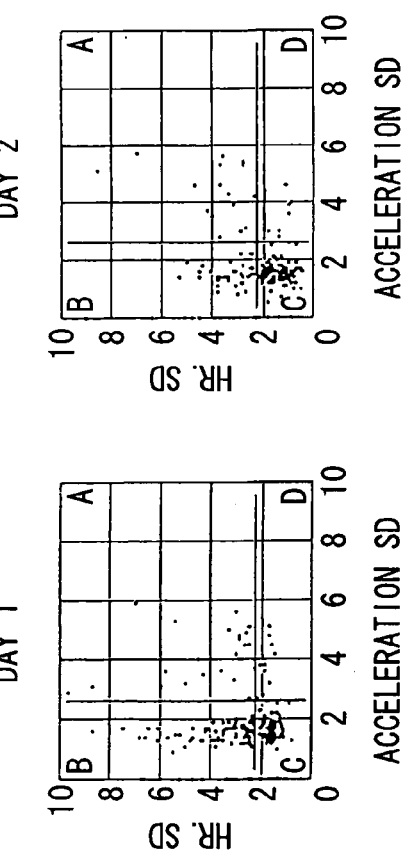
FIG. 9D is a graph showing a distribution of the driver's degree of activity according to the present invention.
Figure 9E:
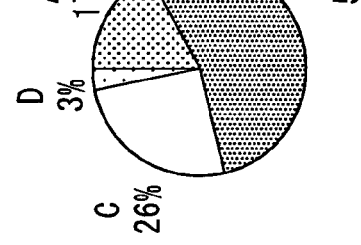
FIG. 9E is a graph showing a distribution of the driver's degree of activity according to the present invention.
Figure 9F:
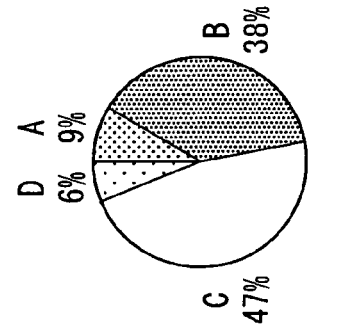
FIG. 9F is a graph showing a distribution of the driver's degree of activity according to the present invention.
Figure 9G:
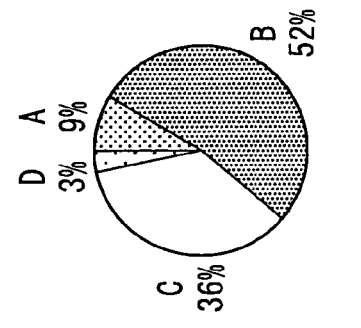
FIG. 9G is a graph showing a distribution of the driver's degree of activity according to the present invention.
Figure 9H:
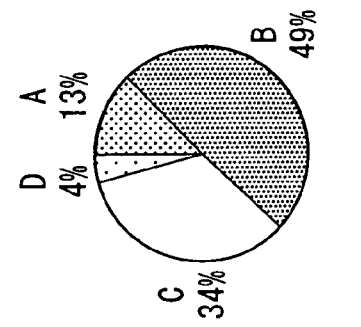
FIG. 9H is a graph showing a distribution of the driver's degree of activity according to the present invention.

As shown in a flowchart of FIG. 8, in step S100, the ECU 1 determines threshold values in the life information and a time information based on the second vehicle information and the second life information as shown in FIG. 6 with a formula such as the above-described (1). The time information threshold value can be a predetermined one.

Next, in step S110, the ECU 1 calculates indicators such as standard divisions of the first vehicle information (the vehicle's velocity and acceleration) and the first life information (the driver's heart rate) during one minute. Thus, the ECU 1 sequentially generates data of the analytic segment of one minute.

In step S120, the ECU 1 determines the driver's activity decree (the quadrant) by comparing the data of the analytic segment of one minute calculated in the Step S110 and the threshold values of the life information and the time information.

That is, the ECU 1 determines in which quadrant among those of A to D the data of the first life information (such as the standard division of the vehicle's acceleration A.SD) and the first life information (such as the standard division of the driver's heart rate HR.SD) based on the threshold values of the life information and the vehicle information.

In step S130, the ECU 1 determines the continuation time in which the driver's condition remains (or a frequency in which the driver's condition is). Here, the quadrants C and D are considered to be a quadrant.

In step S140, the ECU 1 determines whether the continuation time in which the driver's condition remains (or the frequency in which the driver's condition is) is over the time threshold value or not. If Yes in the Step S140, the process goes to Step S150. If No in the Step S140, the process goes to Step 160.

In step S150, it is considered to be in a state that the driver's condition is in a low activity not suitable for driving because the driver's condition continued in the quadrants C and D more than the time threshold values. Thus, the ECU 1 generates an alarm 11 to inform the cautious state to the driver.

In step S160, the ECU 1 determines whether the detection is finished or not such by a driver's operation of a switch to indicate the detection end. If Yes in the step S160, the process goes to step S170. If No in step S160, the process returns to the above-described step S100 and repeats the steps S100 to S160 again.

In step S170, the ECU 1 calculates the shares of the respective quadrants, displays the calculation results such as values and the graphs shown in FIG. 9E to 9H on a display and terminates the process.

(d) The advantages of this embodiment will be described.
i) In this embodiment, by using the second life information and by using the second vehicle information, the threshold values (the life information threshold value and the time domain threshold value) are determined to investigate the driver's degree of activity.

Further, the ECU 1 obtains the driver's heart rate as the first life information and the vehicle's velocity and acceleration as the first vehicle information. Then the ECU 1 determines in which quadrant the data of the first life information and the first vehicle information is.

Furthermore, the ECU 1 calculates the duration time during which the data of the first life information and the first vehicle information remains in each of the quadrants A-D. The ECU 1 determines whether the duration time in which the data of the first life information and the first vehicle information remains in the quadrants C or D is over the time domain threshold value. When the duration time is over the time domain threshold value, the ECU 1 generates an alarm to notify the driver the cautious state.

Thus, this embodiment has a remarkable advantage in detecting the degree of driver's activity with high accuracy.

Still further, the ECU 1 can set and adjust the life information threshold value and the vehicle information threshold value in accordance with the second life information and the second vehicle information. Thus, this embodiment has a further advantage in detecting the degree of driver's activity with still high accuracy by including respective driver's tendency in the degree of activity.

ii) An example of data obtained by the above-described calculation will be described referring to FIGS. 9A-9H. The data shown in FIGS. 9A-9H includes the life information and the vehicle information obtained by driving a given route for four days.

The marks shown in FIGS. 9A to 9D are data of each analytic segment for one minute on the first to fourth day. FIGS. 9E to 9H depicts the distribution of the data classified into the quadrant A to D.

According to the data, the driver's activity on the second day is lower than those of the other days.

(e) The applications of the present invention will be described in the following.

Figure 10:
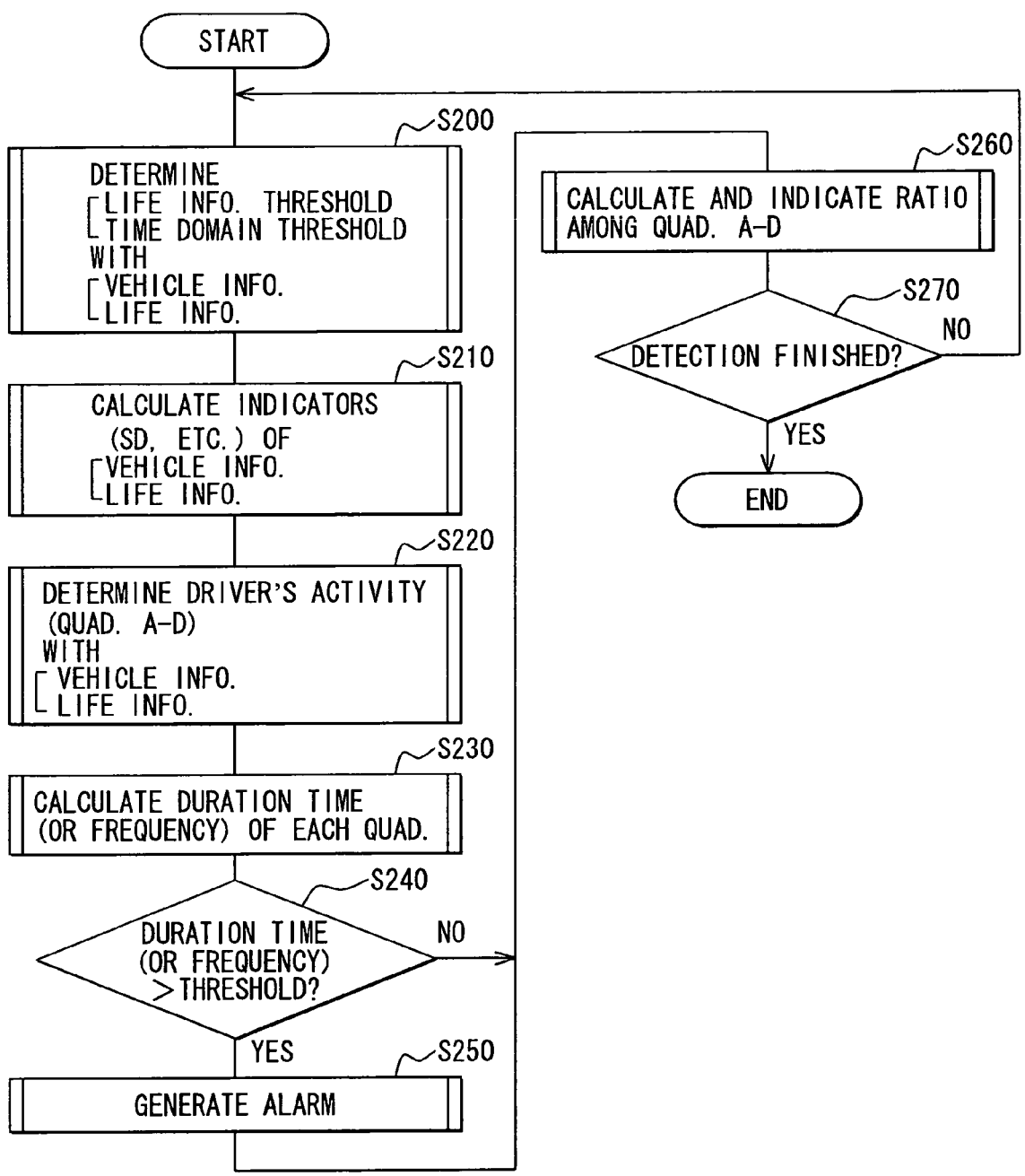
FIG. 10 is a flowchart showing a process of the driver's condition detector for a vehicle according to another embodiment of the present invention.

1) For instance, the above-described process shown in FIG. 8 can be substituted by another process shown in a flowchart of FIG. 10. The process of steps S200-S250 is as same as the process of steps S100-S 50 in FIG. 8. In this application, the ECU 1 calculates shares of the quadrants A to D and displays the shares in step S260, then determines the finish of the measure in step S270 as same as the above-described step S160.

That is, the process shown in FIG. 10 calculates the shares of the quadrants A to D in real time and calculates and displays those shares in the preceding several minutes before the finish of the measure.

Figure 11A:
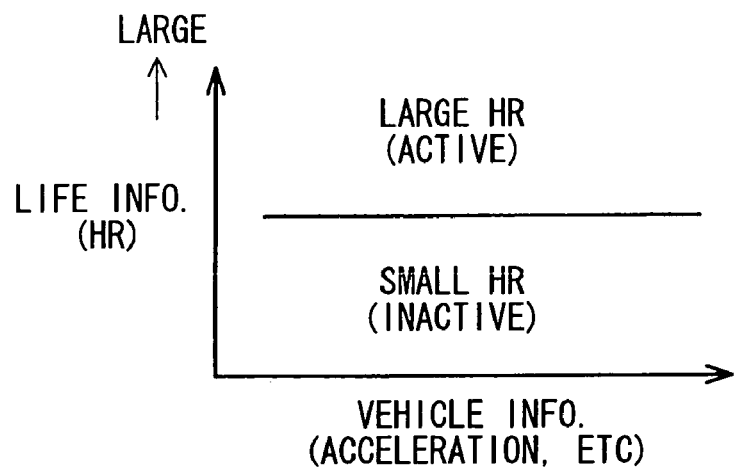
FIG. 11A is a schematic diagram showing a classification of the driver's degree of activity according to still another embodiment.
Figure 11B:
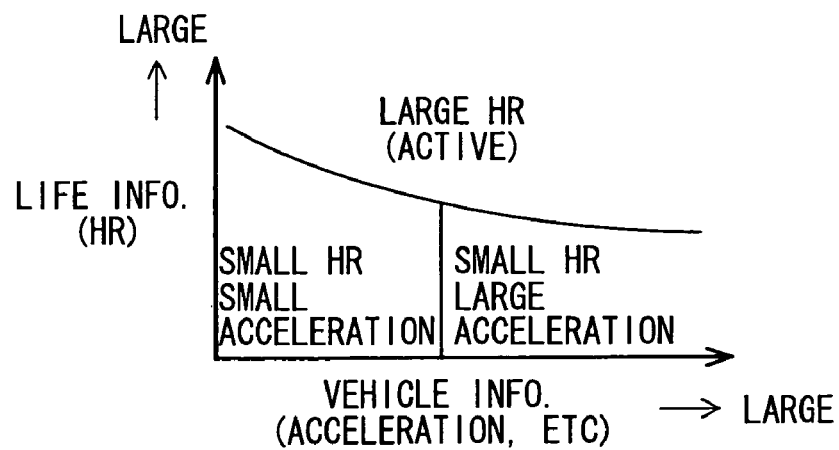
FIG. 11B is a schematic diagram showing a classification of the driver's degree of activity according to a further embodiment.

2) By using only the first life information such as the driver's heart rate, the domain may be classified into two as shown in FIG. 11A. By using the first life information and the first vehicle information, the domain is classified into three as shown in FIG. 11B.

3) The driver's heart rate can be obtained not only by the optical pulse wave meter, but by a heart rate meter installed in a steering wheel of the vehicle and by a pressures sensor installed in the driver's seat.

4) In a case of modifying the threshold values of the life information and the time domain to the second life information, the threshold values may be set in accordance with the quality of the driver's last sleep.

For example, by measuring a driver's last sleeping state and the threshold value for the standard division of the driver's heart rate HR.SD may be determined to be a mean value of the standard division of the driver's heart rate HR.SD in non-REM sleeps in the driver's last sleeping state. Specifically, when the standard division of the driver's heart rate in the non-REM sleep SD is S, the threshold value for the driver's heart rate in the driving may be set to c×S (wherein c is a coefficient).

Further, the threshold values may be set in accordance with an estimation of the driver's condition. For example, when the driver's condition is estimated to be low, it is useful for detecting a decrease of the driver's degree of activity to set the life information threshold value relatively high and to set the time domain threshold value relatively low.

Furthermore, the threshold values may be set in accordance with the daily, weekly and yearly variations of the driver's condition stored in a database. For example, at a nighttime, it is useful for detecting a decrease of the driver's degree of activity to set the life information threshold value relatively high and to set the time domain threshold value relatively low.

This description of the invention is merely exemplary in nature and, thus, variations that do not depart from the gist of the invention are intended to be within the scope of the invention. For example, the above-described functions of the driver's condition detector may be realized by a process executed by a computer program, namely the computer program realizing the above-described functions is included in the present invention.

Such variations are not to be regarded as a departure from the spirit and scope of the invention.

What is claimed is:

1. A driver's condition detector for a vehicle comprising:
a first driver's condition detection device for detecting a first life information indicating a driver's degree of activity;
a vehicle activity detection device for detecting a first vehicle information indication a vehicle's degree of action;
a driver's condition classification device for classifying a two-dimensional map into at least three regions, the two-dimensional map having a first axis representing the first life information and a second axis representing the first vehicle information;

a driver's condition determination device for determining whether a driver's condition is suitable for a driving operation based on a distribution of the first life information in the regions;

a second driver's condition detection device for detecting a second life information indicating the driver's degree of activity other than the first life information; and a second vehicle activity detection device for detecting a second vehicle information indicating the vehicle's degree of action other than the first vehicle information, wherein:

the driver's condition classification device determines a life information threshold based on at least one of the second life information and the second vehicle information and classifies the first life information by the life information threshold;

at least one of the second driver's information and the second vehicle information includes a plurality kinds of information classes; and the driver's condition classification device determines the life information threshold based on the plurality kinds of information classes respectively weighted.

2. The driver's condition detector according to claim 1, wherein:

the first life information includes a data of a driver's heart rate.

3. The driver's condition detector according to claim 1, wherein:

the first life information includes a data of a driver's nerve activity.

4. The driver's condition detector according to claim 1, further comprising a vehicle activity detection device for detecting a first vehicle information indicating a vehicle's degree of action, wherein the driver's condition classification device classifies a combination of the first life information and the first vehicle information into at least three regions.

5. The driver's condition detector according to claim 4, wherein the first vehicle information is any one of:
(1) A.SD;
(2) V.SD;
(3) V.CV=(V.SD/V.Ave)×100;
(4) a×A.SD+b×V.Ave;
(5) a×V.SD+b×V.Ave;
(6) a×V.CV+b×V.Ave;
(7) k×A.SD×V.Ave; and
(8) k×V.SD×V.Ave,
wherein A.SD denotes a standard division of a vehicle's acceleration, V.SD denotes a standard division of a vehicle's velocity, V.CV denotes a coefficient of a vehicle's velocity variation, V.Ave denotes a vehicle's average velocity, a and b denote weightings and k denotes a coefficient.

6. The driver's condition detector according to claim 1, wherein the life information threshold is determined based on the second vehicle information.

7. The driver's condition detector according to claim 1, wherein the life information threshold is determined based on the second vehicle information.

8. The driver's condition detector according to claim 1, further comprising a frequency detector for detecting a frequency information for the first life information to be in at least one of the regions, wherein the driver's condition classification device classifies the frequency information into at least two regions.

9. The driver's condition detector according to claim 8, wherein the frequency information includes a time for the first life information to be in the at least one of the regions.

10. The driver's condition detector according to claim 8, wherein the driver's condition classification device determines the time domain threshold based on the second vehicle information.

11. The driver's condition detector according to claim 8, wherein the driver's condition classification device determines the time domain threshold based on the second life information.

12. The driver's condition detector according to claim 1, further comprising an alarm generator for generating an alarm when the driver's condition determination device determines the driver's condition is not suitable for the driving operation.

13. The drivers condition detector according to claim 1, wherein the first life information is any one of:
(1) HR.SD;
(2) HR.CV=(HR.SD/HR.Ave)×100;
(3) a×HR.SD+b×HR.Ave;
(4) a×HR.SD+b×(HR.Ave−HR.Ave');
(5) k×HR.SD×HR.Ave; and
(6) k×HR.SD×(HR.Ave−HR.Ave'),
wherein HR.SD denotes a standard division of a driver's heart rate, HR.CV denotes a coefficient of a variation of the driver's heart rate, HR.Ave denotes an average of the driver's heart rate, a and b denote weightings, HR.Ave' denotes another average of the driver's average heart rate at a predetermined condition and k denotes a coefficient.

14. The driver's condition detector according to claim 1, wherein the driver's condition determination device determines that the driver's condition is bad when the first life information is out of a predetermined region.

15. The driver's condition detector according to claim 14, wherein the predetermined range is HR.Ave+k×HR.SD, wherein HR.SD denotes a standard division of a driver's heart rate, HR.Ave denotes an average of the driver's heart rate, and k denotes a coefficient.

16. The driver's condition detector according to claim 1, wherein the driver's condition determination device determines that the driver's condition is bad when the first life information is continuously in a predetermined region previously registered when the driver was in a bad condition.

17. The driver's condition detector according to claim 1, wherein the driver's condition determination device calculates the shares of the first life information distributed into the regions and displays the shares.

18. A computer program carried on a computer readable medium, the computer program for realizing the driver's condition detector according to claim 1 when read and executed on a computer.

19. A driver's condition detector for a vehicle comprising:

a first driver's condition detection device for detecting a first life information indicating a driver's degree of activity;

a driver's condition classification device for classifying the first life information into at least two regions; and a driver's condition determination device for determining whether a driver's condition is suitable for a driving operation based on a distribution of the first life information in the regions, wherein the driver's condition determination device determines that the driver's condition is bad when the first life information is out of a predetermined range of HR.Ave+k×HR.SD, wherein HR.SD denotes a standard division of a driver's heart rate, HR.Ave denotes an average of the driver's heart rate, and k denotes a coefficient.

20. A driver's condition detector for a vehicle comprising:
a first driver's condition detection device for detecting a first life information indicating a driver's degree of activity;
a driver's condition classification device for classifying the first life information into at least two regions;
a driver's condition determination device for determining whether a driver's condition is suitable for a driving operation based on a distribution of the first life information in the regions;
a second driver's condition detection device for detecting a second life information indicating the driver's degree of activity other than the first life information; and
a second vehicle activity detection device for detecting a second vehicle information indicating the vehicle's degree of action other than the first vehicle information, wherein:
  the driver's condition classification device determines a life information threshold based on at least one of the second life information and the second vehicle information and classifies the first life information by the life information threshold,
  at least one of the second driver's information and the second vehicle information includes a plurality kinds of information classes; and
  the driver's condition classification device determines the life information threshold based on the plurality kinds of information classes respectively weighted.

21. A driver's condition detector for a vehicle comprising:
a first driver's condition detection device for detecting a first life information indicating a driver's degree of activity;
a vehicle activity detection device for detecting a first vehicle information indication a vehicle's degree of action;
a driver's condition classification device for classifying a two-dimensional map into at least three regions, the two-dimensional map having a first axis representing the first life information and a second axis representing the first vehicle information;
a driver's condition determination device for determining whether a driver's condition is suitable for a driving operation based on a distribution of the first life information in the regions,
wherein the driver's condition determination device determines that the driver's condition is bad when the first life information is out of a predetermined range including HR.Ave+k×HR.SD, wherein HR.SD denotes a standard division of a driver's heart rate, HR.Ave denotes an average of the driver's heart rate, and k denotes a coefficient.

22. The driver's condition detector according to claim 21, wherein:
the first life information includes a data of a driver's heart rate.

23. The driver's condition detector according to claim 21, wherein:
the first life information includes a data of a driver's nerve activity.

24. The driver's condition detector according to claim 21, further comprising a vehicle activity detection device for detecting a first vehicle information indicating a vehicle's degree of action, wherein the driver's condition classification device classifies a combination of the first life information and the first vehicle information into at least three regions.

25. The driver's condition detector according to claim 24, wherein the first vehicle information is any one of:
(1) A.SD;
(2) V.SD;
(3) V.CV=(V.SD/V.Ave)×100;
(4) a×A.SD+b×V.Ave;
(5) a×V.SD+b×V.Ave;
(6) a×V.CV+b×V.Ave;
(7) k×A.SD×V.Ave; and
(8) k×V.SD×V.Ave,
wherein A.SD denotes a standard division of a vehicle's acceleration, V.SD denotes a standard division of a vehicle's velocity, V.CV denotes a coefficient of a vehicle's velocity variation, V.Ave denotes a vehicle's average velocity, a and b denote weightings and k denotes a coefficient.

26. The driver's condition detector according to claim 21, further comprising:
a second driver's condition detection device for detecting a second life information indicating the driver's degree of activity other than the first life information; and
a second vehicle activity detection device for detecting a second vehicle information indicating the vehicle's degree of action other than the first vehicle information, wherein
the driver's condition classification device determines a life information threshold based on at least one of the second life information and the second vehicle information and classifies the first life information by the life information threshold.

27. The driver's condition detector according to claim 26, wherein:
at least one of the second driver's information and the second vehicle information includes a plurality kinds of information classes; and
the driver's condition classification device determines the life information threshold based on the plurality kinds of information classes respectively weighted.

28. The driver's condition detector according to claim 21, wherein the life information threshold is determined based on the second vehicle information.

29. The driver's condition detector according to claim 21, wherein the life information threshold is determined based on the second vehicle information.

30. The driver's condition detector according to claim 21, further comprising a frequency detector for detecting a frequency information for the first life information to be in at least one of the regions, wherein the driver's condition classification device classifies the frequency information into at least two regions.

31. The driver's condition detector according to claim 30, wherein the frequency information includes a time for the first life information to be in the at least one of the regions.

32. The driver's condition detector according to claim 30, wherein the driver's condition classification device determines the time domain threshold based on the second vehicle information.

33. The driver's condition detector according to claim 30, wherein the driver's condition classification device determines the time domain threshold based on the second life information.

34. The driver's condition detector according to claim 30, further comprising an alarm generator for generating an alarm when the driver's condition determination device determines the driver's condition is not suitable for the driving operation.

35. The drivers condition detector according to claim 21, wherein the first life information is any one of:
(1) HR.SD;
(2) HR.CV=(HR.SD/HR.Ave)×100;
(3) a×HR.SD+b×HR.Ave;
(4) a×HR.SD+b×(HR.Ave−HR.Ave');
(5) k×HR.SD×HR.Ave; and
(6) k×HR.SD×(HR.Ave−HR.Ave'),
wherein HR.SD denotes a standard division of a driver's heart rate, HR.CV denotes a coefficient of a variation of the driver's heart rate, HR.Ave denotes an average of the driver's heart rate, a and b denote weightings, HR.Ave' denotes another average of the driver's average heart rate at a predetermined condition and k denotes a coefficient.

36. The driver's condition detector according to claim 21, wherein the driver's condition determination device calculates the shares of the first life information distributed into the regions and displays the shares.

37. A computer program carried on a computer readable medium, the computer program for realizing the driver's condition detector according to claim 21 when read and executed on a computer.

38. An article of manufacture comprising a computer readable medium and instructions carried on the medium, the instructions when executed on a computer for causing the computer to:
- detect a first life information indicating a driver's degree of activity;
- detect a first vehicle information indication a vehicle's degree of action;
- classify a two-dimensional map into at least three regions, the two-dimensional map having a first axis representing the first life information and a second axis representing the first vehicle information;
- determining whether a driver's condition is suitable for a driving operation based on a distribution of the first life information in the regions; and
- determine that the driver's condition is bad when the first life information is out of a predetermined range including HR.Ave±k×HR.SD, wherein HR.SD denotes a standard division of a driver's heart rate, HR.Ave denotes an average of the driver's heart rate, and k denotes a coefficient.

* * * * *